(12) United States Patent
Thalgott

(10) Patent No.: US 7,226,480 B2
(45) Date of Patent: *Jun. 5, 2007

(54) DISC PROSTHESIS

(75) Inventor: John S. Thalgott, Las Vegas, NV (US)

(73) Assignee: Depuy Spine, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/260,677

(22) Filed: Sep. 27, 2002

(65) Prior Publication Data

US 2003/0023312 A1    Jan. 30, 2003

Related U.S. Application Data

(63) Continuation-in-part of application No. 09/646,169, filed on Sep. 14, 2000, now Pat. No. 6,458,159.

(51) Int. Cl.
*A61F 2/44*    (2006.01)
*A61F 2/30*    (2006.01)

(52) U.S. Cl. .................... 623/17.11; 623/17.16

(58) Field of Classification Search ............. 623/17.11, 623/17.12, 17.13, 17.14, 17.15, 17.16; 606/61
See application file for complete search history.

(56) References Cited

U.S. PATENT DOCUMENTS

| | | | |
|---|---|---|---|
| 4,349,921 A | 9/1982 | Kuntz | |
| 4,479,491 A | 10/1984 | Martin | |
| 4,497,075 A | 2/1985 | Niwa et al. | |
| 4,655,777 A | 4/1987 | Dunn et al. | |
| 4,714,469 A | 12/1987 | Kenna | |
| 4,759,766 A | 7/1988 | Buettner-Janz et al. | |
| 4,863,476 A | 9/1989 | Shepperd | |
| 4,863,477 A | 9/1989 | Monson | |
| 4,874,389 A | 10/1989 | Downey | |
| 4,904,261 A | 2/1990 | Dove et al. | |
| 4,911,718 A | 3/1990 | Lee et al. | |
| 4,917,704 A | 4/1990 | Frey et al. | |
| 4,932,969 A | 6/1990 | Frey et al. | |

(Continued)

FOREIGN PATENT DOCUMENTS

EP    0 646 366    4/1995

(Continued)

*Primary Examiner*—Pedro Philogene
(74) *Attorney, Agent, or Firm*—Robert D. Katz; Cooper & Dunham LLP

(57) ABSTRACT

The invention provides a spinal disc implant comprising two side walls which are opposed and substantially parallel spaced apart by a front wall and a back wall to define an interior space. The side walls define substantially elliptical curves joining the front and back walls. The front wall is also curved and the back wall may be either curved or straight. The walls may have openings or holes which may be circular or elliptical in shape. The upper and lower edges of the implant have a plurality of teeth extending therefrom for engaging adjacent vertebrae. The implant is made of a biocompatible metal such as titanium or an alloy thereof, and the first and second sides tapering from the second end to the first end. The interior space has a porous hydroxyapatite block shaped to fill the interior space. The porous hydroxyapatite substance helps the prosthesis integrate into the vertebral structure by allowing into the pores.

12 Claims, 1 Drawing Sheet

U.S. PATENT DOCUMENTS

| | | | |
|---|---|---|---|
| 4,936,848 | A | 6/1990 | Bagby |
| 4,946,378 | A | 8/1990 | Hirayama et al. |
| 4,955,908 | A | 9/1990 | Frey et al. |
| 4,961,740 | A | 10/1990 | Ray et al. |
| 4,997,432 | A | 3/1991 | Keller |
| 5,002,576 | A | 3/1991 | Fuhrmann et al. |
| 5,035,716 | A | 7/1991 | Downey |
| 5,047,055 | A | 9/1991 | Bao et al. |
| 5,055,104 | A | 10/1991 | Ray |
| 5,071,437 | A | 12/1991 | Steffee |
| 5,108,438 | A | 4/1992 | Stone |
| 5,123,926 | A | 6/1992 | Pisharodi |
| 5,171,281 | A | 12/1992 | Parsons et al. |
| 5,192,326 | A | 3/1993 | Bao et al. |
| 5,192,327 | A | 3/1993 | Brantigan |
| 5,258,043 | A | 11/1993 | Stone |
| 5,306,308 | A | 4/1994 | Gross et al. |
| 5,306,309 | A | 4/1994 | Wagner et al. |
| 5,314,477 | A | 5/1994 | Marnay |
| 5,314,478 | A | 5/1994 | Oka et al. |
| 5,320,644 | A | 6/1994 | Baumgartner |
| 5,370,697 | A | 12/1994 | Baumgartner |
| 5,401,269 | A | 3/1995 | Buttner-Janz et al. |
| 5,716,415 | A * | 2/1998 | Steffee ............... 623/17.16 |
| 5,865,845 | A * | 2/1999 | Thalgott ............. 623/17.16 |
| 5,888,224 | A * | 3/1999 | Beckers et al. ..... 623/17.16 |
| 5,888,227 | A * | 3/1999 | Cottle ................. 623/17.16 |
| 5,989,289 | A * | 11/1999 | Coates et al. ....... 623/17.16 |
| 6,113,638 | A | 9/2000 | Williams et al. |
| 6,136,031 | A | 10/2000 | Middleton |
| 6,143,032 | A | 11/2000 | Schafer et al. |
| 6,241,771 | B1 * | 6/2001 | Gresser et al. ..... 623/17.16 |
| 6,245,108 | B1 | 6/2001 | Biscup |
| 6,458,159 | B1 * | 10/2002 | Thalgott ............. 623/17.11 |
| 6,482,233 | B1 * | 11/2002 | Aebi et al. ......... 623/17.11 |
| 6,635,086 | B2 * | 10/2003 | Lin ..................... 623/17.11 |
| 6,964,687 | B1 * | 11/2005 | Bernard et al. ..... 623/17.16 |

FOREIGN PATENT DOCUMENTS

| | | |
|---|---|---|
| WO | WO 95/08306 | 3/1995 |
| WO | WO 97/15248 | 5/1997 |

\* cited by examiner

DISC PROSTHESIS

CROSS-REFERENCE TO RELATED APPLICATION

This application is a continuation-in-part of U.S. patent application Ser. No. 09/646,169 filed on Sep. 14, 2000, now U.S. Pat. No. 6,458,159 B1, issued on Oct. 1, 2002.

FIELD OF THE INVENTION

This invention relates to artificial biocompatible synthetic vertebral prostheses, and more particularly to prosthetic metal intervertebral discs.

BACKGROUND OF THE INVENTION

Many types of vertebral prostheses have been proposed and patented for implantation in the vertebral disc space after surgical removal of a diseased or damaged disc. Such devices fall into three broad categories. One category of prostheses includes the use of pliable synthetic materials in an attempt to mimic the compressibility of the human spinal disc. For example, U.S. Pat. No. 5,171,281 (Parsons) discusses a disc spacer which purports to possess mechanical properties akin to those of the normal disc by varying the hardness of the elastomeric material in its nucleus and annulus. U.S. Pat. No. 5,192,326 (Bao) illustrates a prosthetic disc formed from a multiplicity of hydrogel beads having a water content of at least 30%. According to the patent, a semi-permeable membrane covers the beads and is said to permit fluids to flow in and out of the prosthetic nucleus. U.S. Pat. No. 5,071,437 (Steffee) proposes another approach to a pliable

SUMMARY OF THE INVENTION

The foregoing objects are achieved and the disadvantages of the prior art are overcome by providing a spinal disc implant comprising an implant of a biocompatible metallic body having a front wall, a rear wall, and two side walls extending therebetween to define an interior space. Each side wall defines a substantially arcuate curve joining one end of the front wall and one end of the rear wall. Further, each wall contains at least one opening therein, and the upper and lower surfaces of the two side walls having a plurality of teeth extending therefrom for engaging adjacent vertebral bodies. The side walls of the implant taper in height from the rear wall to the front wall; and the front wall and the rear wall each lack teeth, and have a height substantially similar to that of a portion of the side wall adjacent the front and rear walls. The implant is made of a biocompatible metal such as titanium or an alloy thereof, and the first and second sides taper from the junction between the back wall and the side wall to the junction between the front wall and the side wall. Preferably, the interior space includes a porous hydroxyapatite block shaped and press fit, cemented or screwed in to fill the interior space. The porous hydroxyapatite substance helps the prosthesis integrate into the vertebral structure by allowing bone to grow into pores.

BRIEF DESCRIPTION OF THE DRAWINGS

Other features and advantages of the invention will be apparent from the following detailed description of the preferred embodiments taken in conjunction with the accompanying drawings as follows.

DETAILED DESCRIPTION OF THE PREFERRED EMBODIMENTS

Figure 1:
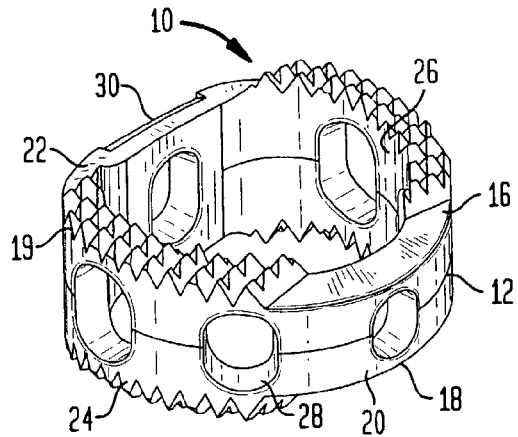
FIG. 1 shows a perspective view of one embodiment of the spinal disc implant of the present invention.

FIG. 1 illustrates a spinal disc implant of the present invention, generally indicated by the reference numeral 10. The implant 10 has a generally D-shaped body 12 including a central opening 14. The implant further includes upper and lower faces 16, 18 having a plurality of teeth 19 or other gripping means included on each face. The implant 10 has a front wall 20, a back wall 22, and first and second side walls 24, 26, which are all joined. The back wall 22 is relatively straight, while the front wall 20 and side walls 24 and 26 are curved. The openings or holes 28 in the walls are preferably of an elliptical shape, although they may be square, circular, or rectangular. The embodiment of FIG. 1 has a hole or opening 28 in the center of the back wall 18 and in the center of the front wall 20. There is an opening or hole 28 at the junction between each side wall 24, 26 and the front wall 20, as well as in the approximate center of each side wall 24, 26 for a total of six openings or holes 28 in the implant 10. Teeth 19 appear on the upper or lower surfaces 16,18 of the side walls 24, 26, but not on the upper or lower surfaces of the front and rear walls 20, 22. The upper and lower surfaces 30, 32 of the rear wall 22 includes notches 34, 36 to provide a structure to engage a gripping tool (not shown) to aid in placement of the implant 10 in the intervertebral space. The space defined by the central opening 14 (best viewed in FIG. 2) openings are preferably filled with hydroxyapatite combined with any biological factor or composition which helps to induce growth of bone and cartilage against the surface of the implant and in the spaces defined by the teeth 19.

Figure 2:
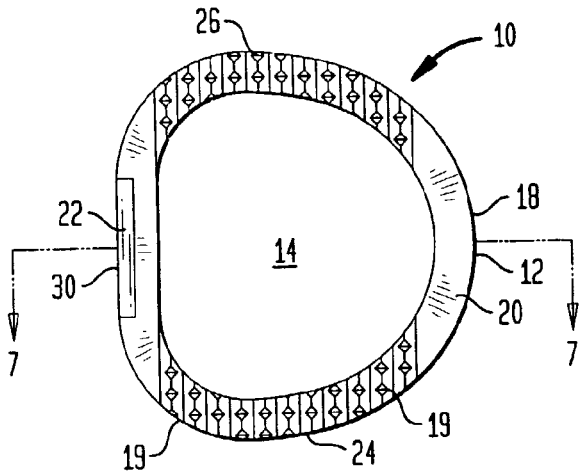
FIG. 2 is a top view of the spinal disc implant of FIG. 1.
Figure 5:
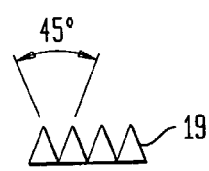
FIG. 5 is a schematic cross-sectional view of the teeth of the implant shown in FIG. 1.
Figure 6:
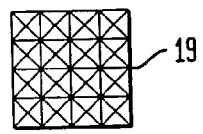
FIG. 6 is a top view of a portion of the teeth on an upper surface of the implant.
Figure 7:
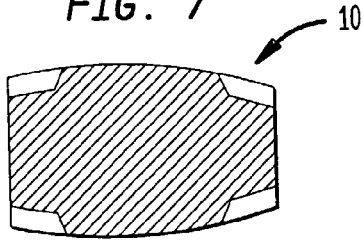
FIG. 7 is a cross-sectional view of the implant of FIG. 1, taken along line 7—7 (before boring the central opening or machining the teeth).

The teeth 19 (shown in FIGS. 1 and 5) are preferably steeply sloped four-sided pyramids of approximately 0.08 inches in height. They are preferably arranged in straight rows across and down the upper and lower faces 16, 18 of the side walls 24, 26 of the implant 10, as shown in FIG. 2. The pyramidal faces of each tooth 19 preferably form a 45° angle with the vertical. They can be formed by machining the implant 10, or as part of the casting process.

Figure 3:
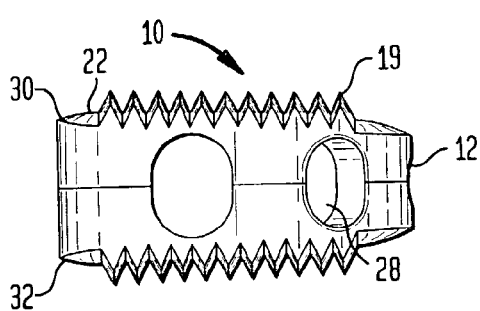
FIG. 3 is a side view of a representative side of the spinal disc implant of FIG. 1.
Figure 4:
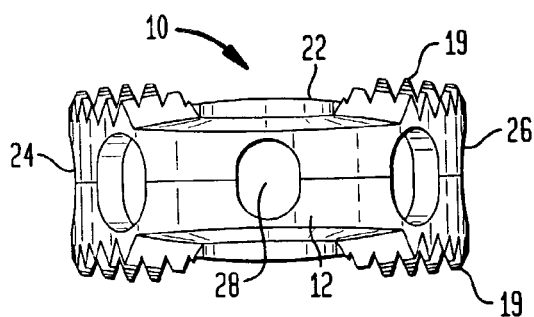
FIG. 4 is a front view of the spinal disc implant of FIG. 1.

An important aspect of the present invention is its geometric compatibility with its environment. Referring to FIGS. 1 and 3, the implant 10 slopes from the rear wall 22 to the front wall 20. This shape enables the implant 10 to fit between adjacent vertebral bodies (not shown) when the spine is in an upright position. The exact angle formed at the vertex defined by the top and bottom faces varies depending on which disc is being replaced. In the lumbar region of the spine, for example, the opposed faces adjacent vertebral bodies define an angle ranging from about 0 to about 20 degrees. Similarly, since the vertebral body, which engages the first and second faces 16, 18 of the implant 10 from above, has a defined curvature, the implant 10 has a curvature which mimics that of the intervertebral space to allow it to conform to the domed shape of the vertebral body surface.

The implant 10 is preferably made from pure titanium or an alloy thereof, preferably anodized to increase its biocompatibility by making it more inert. The implant 10 may be made from bar stock, or tubing or by molding, or from titanium powder using powder metallurgy techniques. The dimensions of the implant 10 vary depending on where in the spine the implant will be inserted. The vertebral bodies in the lumbar area of spine, for example, are larger than the vertebral bodies in the thoracic area. Therefore, an implant intended for the thoracic region would be smaller than one for the lumbar region. Likewise, lower lumbar disc replacements would be larger than upper ones. By way of example, an implant sized for implantation between the third and fourth lumbar vertebrae may have approximate dimensions of 2.7 cm long, 2.5 cm wide, about 2 cm high anteriorly, and would slope down to about 1.3 cm high posteriorly. The slope from rear to front in a typical implant increases by about 3 mm. A person of ordinary skill could adapt the basic dimensions of the implant 10 to make the implant 10 suitable for the space formerly occupied by the particular vertebral disc which needs replacement. The present invention therefore includes implants having varying angles and dimensions to allow implantation at different levels of the spine.

The shape and curvature of the implant 10 provide several advantages. In the lumbar region of the spine, the discs and vertebral bodies are held at an angle creating a lordosis or curvature of the lumbar spine. To have the implant 10 parallel or coplanar would be physiologically and anatomically unacceptable. The natural discs in the lumbar spine are wider anteriorly than they are posteriorly. The disc replacement implant 10 of the present invention is therefore also wider posteriorly than it is anteriorly. This recreates the natural anatomic curvature of the spine.

Further, the implant 10 of the present invention takes into consideration the anatomy of the undersurface of the vertebral body or end plate of the vertebra on which the lower face of the implant 10 rests. The end plate is made of very compact bone circumferentially, but as the bone centralizes towards the middle, it becomes thinner. The thinner portion is dome shaped, and is responsible for the hydraulic stress middle of the end plate. This shape is mimicked by the secondary curvature in the disc implant of the present invention. The secondary arc which corresponds to the dome in the vertebral body provides a mechanism to lock the cage in place and prevent slippage or extrusion. The teeth 19 disposed on portions of the top and bottom faces of the side walls 24, 26 of the implant 10 grip the vertebral body and cause a mechanical interface between the prosthesis and the end plate of the vertebral body.

Preferably, the implant 10 optionally includes an insert of synthetic bone material, such as porous hydroxyapatite or other equivalent substance. Preferably, the synthetic bone material is Interpore ProOsteon 500 brand of porous coralline hydroxyapatite, available from Interpore Cross International, Irvine, Calif. The porous synthetic bone material is held in place by press fit (friction), or by set screws on the sides of the implant 10 (not shown). The porous synthetic bone allows independent placement of the implant 10 into the intervertebral disc space without use of a bone graft. This will help reduce morbidity and complications associated with harvesting a bone graft from the patient, reported to be as high as 21%. It will also obviate the need for use of an allograft, which carries the risk of disease transmission and added expense.

The implant 10 provides a non-articulating disc prosthesis which can be provided in multiple sizes depending on the size needed for the specific lumbar region, and can be furnished in smaller sizes for the cervical and thoracic spine, as miniature cages for placement using endoscopic techniques for minimally invasive spine surgery.

In addition to titanium or a biocompatible alloy thereof, or other biocompatible metal or alloy known to those of skill in the art, the implant of the present invention may be made of other biomaterials including biocompatible metals, metal alloys, ceramics, and polymers or combinations thereof, having suitable hardness and strength characteristics. For example, the implant may be made of a synthetic biocompatible material, as disclosed in U.S. Pat. No. 5,306,309 (Wagner); U.S. Pat. No. 5,192,327 (Brantigan); U.S. Pat. No. 5,171,281 (Parsons); U.S. Pat. No. 4,911,718 (Lee); and U.S. Pat. No. 4,655,777 (Dunn). The entire contents of the foregoing references is incorporated herein by reference. Of particular interest, in addition to titanium or an alloy thereof, is a fiber reinforced synthetic material, such as a carbon fiber reinforced polymer. The implants may have ceramic portions, facings, or coatings, and may also include or be coated with one or more bone growth inducing factors or compositions. Optionally, the implant may include an elastomeric layer or portion, to add compressibility to the implant.

During implantation surgery, the surgeon exposes the herniated or damaged disc, and removes it. A spinal disc implant 10 (optionally including a central core of porous synthetic bone), is inserted with a tool which grips the implant 10 to enable the surgeon to lift and insert the implant 10 in the intervertebral space defined by adjacent vertebral bodies from which the damaged or diseases disc was removed. The implant 10 is positioned on the vertebral body so that its transverse curvature conforms to the dome shape of the vertebral body. At the same time, the implant 10 is positioned so that its anterior to posterior position will create the proper angulation between vertebrae to help to restore the natural anatomic curvature of the human spine. The implant 10, once implanted, encourages osseointegration in two distinct ways. The teeth 19 form an irregular surface which grip the vertebral body and allow bone tissue to grow in and around the teeth 20. Also, the synthetic porous bone segment, if present, allows bone tissue to grow into the pores, to help anchor the implant 10 in place without resorting to bone grafts orallografts. The advantages to the present implant 10 include the following: (1) the pattern of teeth is different than previous discs; (2) the front of the device fits within the end plates of the vertebral bodies in a much more anatomic fashion as compared with previous discs; and (3) the implant provided herein can be used in the lumbar spine. However, smaller versions for use in the cervical and thoracic spine are intended to be part of the invention.

Various modifications will be apparent to those skilled in the art. Such modifications and changes are intended to be included within the scope of the invention, which is defined by the following claims.

I claim:

1. An implant of a biocompatible metallic body having a front wall, a rear wall, and two side walls extending therebetween to define a substantially D-shaped interior space, and wherein each side wall defines a substantially arcuate curve joining one end of the front wall and one end of the rear wall, and wherein each wall contains at least one opening therein, the upper and lower surfaces of the two side walls having a plurality of teeth of pyramidal shape extending therefrom for engaging adjacent vertebral bodies, the implant being made of a biocompatible metal, the side walls tapering in height from the rear wall to the front wall; wherein the upper and lower surfaces of the front and rear walls each lack teeth, and have a height substantially similar to that of a portion of the side wall adjacent the front and rear walls.

2. A spinal disc implant in accordance with claim 1, wherein the height of the rear wall ranges from about 11 mm to about 15 mm, and the height of the front wall ranges from about 8 mm to about 12 mm.

3. A spinal disc implant in accordance with claim 2, wherein the difference in height between the rear wall of the implant and the front wall of the implant is about 3 mm.

4. A spinal disc implant in accordance with claim 1 wherein the rear wall of the implant has a notch in an upper and lower edge thereof.

5. A spinal disc implant in accordance with claim 1 wherein the biocompatible metallic body is titanium or an alloy thereof.

6. A spinal disc implant in accordance with claim 5 wherein the interior space includes a porous hydroxyapatite block shaped to be held by the implant within the interior space.

7. A spinal implant in accordance with claim 1 wherein upper and lower surfaces of the implant are curved to mate with a domed surface of adjacent end plates of vertebrae between which the implant is inserted.

8. A spinal disc implant in accordance with claim 7, wherein the upper and lower edges of the implant are convexly curved to mate with the surface of adjacent end plates of vertebrae between which the implant is inserted.

9. An implant of a biocompatible metal for replacing a diseased spinal disk, comprising: a generally D-shaped body, the body including a curved front wall, a substantially straight rear wall, and a pair of spaced apart arcuate side walls connecting the front and rear walls, the side walls including a plurality of teeth of pyramidal shape on upper and lower surfaces thereof; the front and rear walls lacking teeth and having a height equal to that of the side walls less approximately twice the height of the teeth; the rear wall also having a notch on an upper and lower edge thereof for engaging an insertion instrument; the side walls sloping from the front wall to the rear wall such that the height of the front wall exceeds the height of the rear wall by about 3 mm.

10. A spinal disc implant in accordance with claim 9, wherein the height of the front wall ranges from about 8 mm to about 12 mm, and the height of the rear wall ranges from about 11 mm to about 15 mm.

11. A spinal disc implant in accordance with claim 10, wherein the biocompatible metal is titanium or an alloy thereof.

12. A spinal disc implant in accordance with claim 11, wherein the implant includes a plurality of openings spaced around the periphery thereof.

* * * * *